US006889401B2

United States Patent
Fattori et al.

(10) Patent No.: US 6,889,401 B2
(45) Date of Patent: May 10, 2005

(54) POWERED TOOTHBRUSH WITH VIBRATING SECTION

(75) Inventors: Joseph Edward Fattori, Mendham, NJ (US); Robert Moskovich, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 246 days.

(21) Appl. No.: 10/107,093

(22) Filed: Mar. 26, 2002

(65) Prior Publication Data

US 2003/0182744 A1 Oct. 2, 2003

(51) Int. Cl.[7] ............................................. A46B 13/00
(52) U.S. Cl. .............................. 15/22.1; 15/28; 15/22.2
(58) Field of Search ........................ 15/28, 22.1, 22.2

(56) References Cited

U.S. PATENT DOCUMENTS

| 3,110,918 | A | | 11/1963 | Tate, Jr. |
| 3,994,039 | A | * | 11/1976 | Hadary ........................ 15/172 |
| 5,259,083 | A | | 11/1993 | Stansbury, Jr. |
| 5,416,942 | A | | 5/1995 | Baldacci et al. |
| 5,524,312 | A | | 6/1996 | Tan et al. |
| 5,625,916 | A | | 5/1997 | McDougall |
| RE35,941 | E | | 11/1998 | Stansbury, Jr. |
| 6,000,083 | A | | 12/1999 | Blaustein et al. |
| 6,151,745 | A | | 11/2000 | Roberts et al. |
| 6,611,984 | B1 | | 9/2003 | Halm |
| 2003/0084524 | A1 | * | 5/2003 | Blaustein et al. |

FOREIGN PATENT DOCUMENTS

| GB | 2317555 | 4/1998 |
| WO | WO 01/60281 A1 | 8/2001 |

* cited by examiner

Primary Examiner—Deborah Jones
Assistant Examiner—Abraham Bahta
(74) Attorney, Agent, or Firm—Harris A. Wolin

(57) ABSTRACT

The head of a toothbrush includes a tuft block having bristles wherein the tuft block is moved in a direction parallel to the outer surface of the head. A second tuft block having bristles is a vibrating section which is moved in and out in a direction perpendicular to the outer surface of the head. If desired, the head may also include a fixed section with fixed bristles. The movement of the first tuft block may be an oscillating rotational movement.

25 Claims, 1 Drawing Sheet

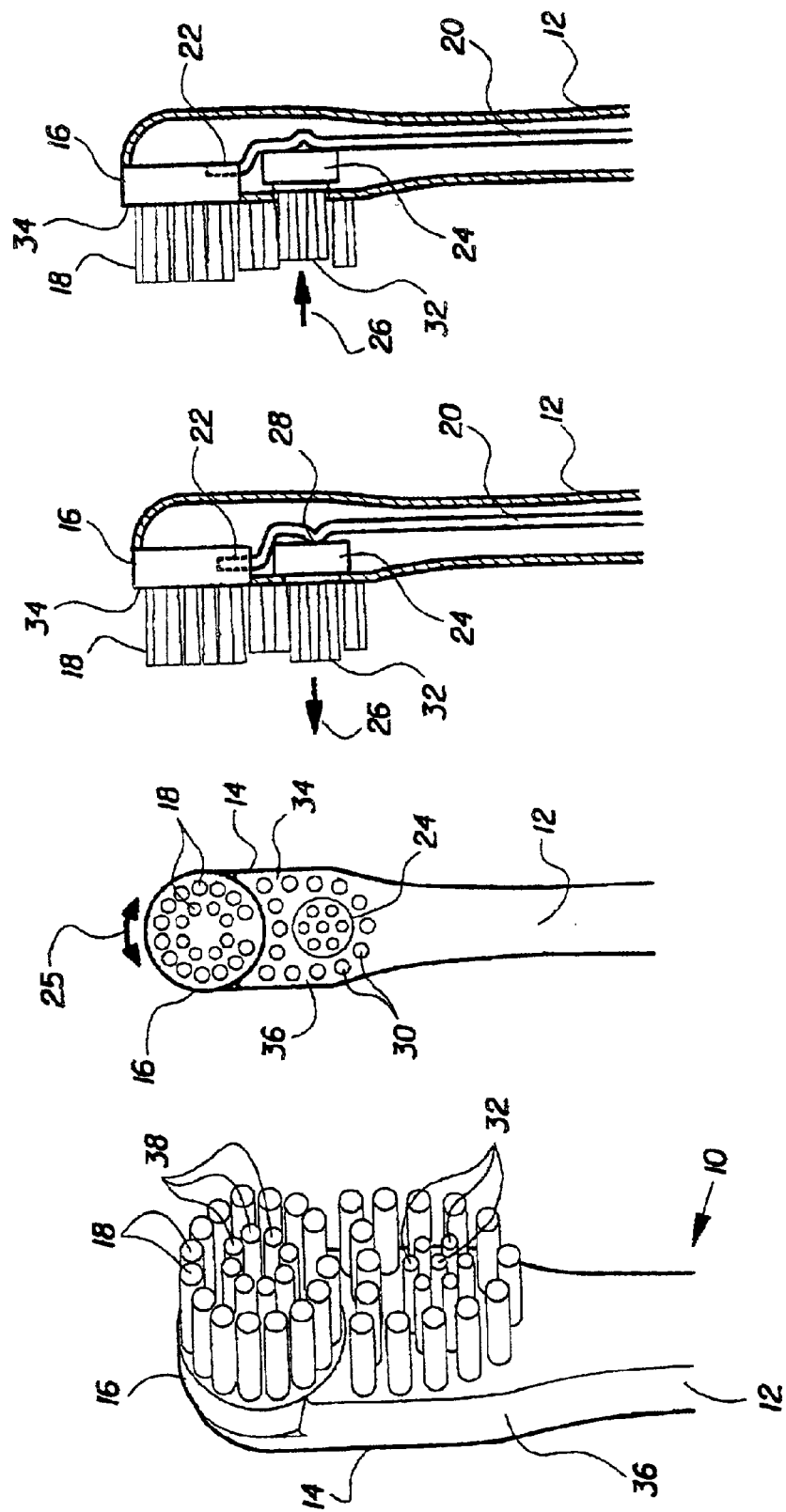

POWERED TOOTHBRUSH WITH VIBRATING SECTION

FIELD OF THE INVENTION

The present invention relates to toothbrushes which include a vibrating section in the head.

BACKGROUND OF THE INVENTION

The present invention is directed to a powered toothbrush and in particular to a toothbrush head having movably mounted bristles. Various types of powered toothbrushes are generally known in the art. Reference is made to U.S. Pat. No. 5,625,916 which relates to an electrically driven toothbrush having a motor drive for rotating a drive shaft. The drive shaft is connected to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

U.S. Pat. No. Re 35,941 discloses a power driven mechanical toothbrush which includes a plurality of side by side tuft blocks extending adjacent to each other in a lateral direction with regard to the longitudinal axis of the toothbrush head. A rotatable motor driven cam shaft extends longitudinally through the head below the sets of tufts blocks. The cam shaft includes a cam surface located at each tuft block. When the cam shaft is rotated the cam surfaces cause the tuft blocks to reciprocate in a direction perpendicular to the cam shaft.

U.S. Pat. No. 3,110,918 discloses a toothbrush having its bristles mounted on a plate which is engaged by a gear mounted on a rotatable rod. Rotation of the rod causes the bristles to move vertically in and out to adjust the effective length of the bristles. The tufts of bristles do not reciprocate during use of the toothbrush. Neither U.S. Pat. No. 3,110,918, nor U.S. Pat. No. Re 35,941 discloses a toothbrush having a second section with movable bristles.

SUMMARY OF THE INVENTION

An object of this invention is to provide a powered toothbrush which includes at least two separate moving sections to deliver a cleaning, polishing, whitening action in addition to the cleaning efficiency of a typical powered toothbrush.

A further object of this invention is to provide such a toothbrush which includes fixed bristles in addition to the different sections having moving bristles.

In accordance with this invention the toothbrush head includes a first tuft block which is mounted for oscillating back and forth in a plane generally parallel to the toothbrush head. At least an additional tuft block is provided for oscillating in a direction generally perpendicular to the tuft head to provide a vibrating section in addition to the first oscillating section. Such a toothbrush may have a replacement, i.e. refill head or a head permanently attached to a handle.

In a preferred practice of this invention the oscillating section is moved back and forth in a rotational direction. The toothbrush head may also include a fixed section having fixed bristles or bristles embedded in an elastomeric material to be independently movable in addition to the bristles on the vibrating head and on the rotationally oscillating head.

In a preferred practice of this invention a single drive shaft is utilized for rotationally oscillating the first tuft block and also for causing the other tuft block to vibrate in a direction perpendicular to the direction of movement of the first tuft block.

THE DRAWINGS

FIG. 1 is a perspective view of a toothbrush head in accordance with this invention;

FIG. 2 is a front elevational view of the head shown in FIG. 1; and

FIGS. 3–4 are side elevational views partly in section of the head shown in FIGS. 1–2 in different phases of operation.

DETAILED DESCRIPTION

FIGS. 1–4 illustrate one practice of this invention wherein a toothbrush 10 includes a neck section 12 of a handle (not shown) and a head 14. The head 14 may be a replaceable, i.e. refill head or may be permanently attached to the brush handle without departing from this invention.

As illustrated the head 14 includes a first tuft block 16 which is illustrated as being at the outermost or distal portion of head 14. Tuft block 16 is preferably a disk of circular cross-section since it is intended to oscillate in a rotational manner. If desired, however, other shapes may be used such as oval or various regular or irregular shapes. A circular shape is preferred since it requires the least amount of clearance to accommodate the oscillating movement.

FIGS. 1 and 2 illustrate a plurality of tufts of bristles 18 mounted on tuft block 16. As shown in FIG. 2 the tufts of bristles 18 are arranged in two sets of coarcuate rows. It is to be understood, however, that other arrangements may also be used.

While FIGS. 1–4 illustrate the bristles to be of conventional fiber form, the term "bristles" is intended to be used in a generic sense as cleaning elements or massage elements and could include, for example, elastomeric fingers or walls arranged in a circular cross-section shape or any type of desired shape, including straight portions or sinusoidal portions.

The bristles could be mounted to the various tuft blocks or sections of head 14 by extending through suitable openings in the tuft block so that the base of the bristles is mounted within or below the tuft block. If desired, the bristles could be embedded in an elastomeric material which would permit the bristles to have an independent motion in addition to the motion imparted by the oscillating tuft block 16 and later described tuft block 24. Similarly, the bristles 30 on other sections of the head 14, such as section 36 could have independent movement, instead of being fixed bristles as on an alternative fixed third section 36, as later described. Such various forms of bristles may thus be used for the bristles referred to or any of the sections of the head 14.

It is to be understood that the specific illustration of the bristles is merely for exemplary purposes. The invention can, however, be practiced with various combinations of the same or different bristle configurations secured to the brush by known technology including staple technology or in-mold tufting technology using the same or different bristle materials (such as nylon bristles, spiral bristles, rubber bristles, etc.) Similarly, while FIGS. 1–4 illustrate the bristles to be generally perpendicular to the outer surface of head 14, some or all of the bristles may be angled at various angles with respect to the outer surface of the bristle head. It is thereby possible to select the combination of bristle configurations, bristle materials and bristle orientations to achieve specific intended results, such as to create as much movement from the oscillating tuft heads to deliver additional oral health benefits like enhanced cleaning, tooth polishing, tooth whitening and/or massaging of the gums.

It is to be understood that the invention can be practiced by locating tufts of bristles in any otherwise open area of the toothbrush head. Such tufts of bristles could be fixed bristles perpendicularly mounted or mounted at an angle to the exposed outer surface 34 of the head 14 or could be bristles mounted on an elastomeric base so as to be independently movable when pressure is applied. Such bristles in their normal condition could be either perpendicular or at an angle to the exposed outer surface of the toothbrush head. Different sets of bristles could be of different colors.

Where a portion of the head contains an outer set of bristles 18 and an inner set of bristle 38, the outer set of bristles may extend further from the tuft block than the inner set of bristles to create a cup-like effect which would facilitate retaining toothpaste on that portion of the head.

As best shown in FIGS. 3–4 a drive shaft 20 extends through handle neck 12. Drive shaft 20 is intended to impart a rotational oscillation to tuft block 16. In a preferred practice of this invention a drive structure could incorporate the type of drive structure illustrated and described in U.S. Pat. No. 5,625,916, all of the details of which are incorporated herein by reference thereto. As described in that patent the drive shaft 20 is rotated by a motor drive. The drive shaft 20 terminates in an offset crank end 22 which is located in a slot or opening in tuft block 16 so that the 360° rotational movement of shaft 20 is transmitted into an oscillating back and forth rotational movement of tuft block 16, as indicated by the arrow 25 in FIG. 2.

FIGS. 1–4 illustrate a further tuft block 24 mounted on head 14 having bristles 32. In the illustrated form only a single tuft block 24 is shown, which is generally circular. In the practice of the present invention, multiple tuft blocks can be used as well as the single tuft block 24, and these blocks or block can be of any other suitable shape as for example egg shape or oval. As later described such multiple blocks or a single block such as tuft block 24 is a moving section which moves in a direction generally perpendicular to the outer surface of the head 14 as illustrated by the arrow 26 in FIGS. 3–4. This in and out reciprocal movement creates a vibrating section that moves in a direction generally perpendicular to the plane of movement of tuft block 16. The vibrating in and out oscillation may be accomplished by providing a raised or cam surface 28 on shaft 20. The raised surface can be a bent portion of shaft 20 or could be a cam member mounted to shaft 20. FIG. 3 shows the tuft block 24 in its maximum extended condition where cam surface 28 is disposed against tuft block 24. The tuft block 24 slides in a bore in the section 36 of head 14. A shoulder on the tuft block 24 retains the tuft block 24 in the head 14. FIG. 4 shows tuft block 24 in its retracted condition.

If desired, a resilient structure such as a spring could be mounted against tuft block 24 to urge the tuft block in a direction opposite the arrow 26 as shown in FIG. 3, thus urging the tuft block against shaft 20. For example, the head 14 would have a bore in which tuft block 24 would freely slide. Head 14 could also have a counterbore for receiving a shoulder on tuft block 24. The spring could be located in the counterbore and act against the shoulder. As a result, as shaft 20 rotates the rotating cam surface 28 would function to overcome the bias of tuft block 24 to move in the direction of arrow 26 in FIG. 3 and the cam surface 28 would thereby cause the tuft block 24 to move in the direction of arrow 26 in FIG. 4.

Although the vibrating section 24 could include some form of spring or biasing means to urge the tuft block 24 in a direction opposite to arrow 26, such positive biasing means is not necessary. Thus, for example, a vibrating affect would still be achieved by use of the cam surface 28 urging the tuft block 24 in the direction of arrow 26 in FIG. 3 and then the tuft block 24 would tend, on its own, to move in a direction opposite arrow 26 when no longer being urged by cam surface 28.

The provision of a cam surface such as cam surface 28 as part of the shaft 20 may utilize the same type of structure as disclosed in U.S. Pat. No. Re 35,941, all of the details of which are incorporated herein by reference thereto. Alternatively, a separate drive mechanism could be provided for each oscillating tuft block 16, 24. The use of the same shaft, however, is advantageous in minimizing parts and space requirements as well as costs.

In operation as shaft 20 rotates its drive end 22 by engagement with a slot (not shown) in tuft block 16 causes the tuft block to oscillate back and forth in the direction of arrow 25 in a plane generally parallel to the outer surface 34 of head 14. While this oscillation occurs cam surface or bent portion 28 of shaft 20 makes initial contact with tuft block 24 and upon continued rotation of shaft 20 the cam surface 28 assumes the position shown in FIG. 3 which urges tuft block 24 to its outermost position in the direction of arrow 26. Continued rotation of shaft 20 causes cam surface 28 to rotate away from tuft block 24 until cam surface 28 no longer contacts tuft block 24. During this continued rotation of cam 20 tuft block 24 is permitted to move back to a position in a direction of arrow 26 shown in FIG. 4.

The invention can also be practiced where multiple or a single tuft block, such as tuft block 24, is a movable tuft block by being free floating. In that regard, shaft 20 would not include any cam surface. Instead, tuft block 24 would be free to move in the direction of arrow 26 between extended and retracted conditions as shown in FIGS. 3 and 4 without any positive drive urging such movement. An advantage of a free floating moving tuft block would be less strain on the motor which drives shaft 20.

As also illustrated the head 14 includes a fixed section 36 having a plurality of non-movable or fixed tufts of bristles 30 which are illustrated as surrounding vibrating tuft block 24. It is again to be understood that such bristles 30 could also be movable by, for example, mounting some or all of the tufts of bristles in an elastomeric material which would cause movement both in response to the bristles contacting the user's teeth, as well as by the vibration caused by the electric brush motor. As also previously described instead of bristles 30 being of normal standard bristle tuft construction, the bristles could be elastomeric fingers, walls, etc. of any desirable size and shape.

In the illustrated embodiment the oscillating tuft block 16 is oscillated back and forth in a rotational direction. The invention could, however, be practiced with other forms of oscillation such as by lateral movement in a direction transverse to the longitudinal axis or the direction of shaft 20 or in a direction parallel to shaft 20. Further, as mentioned above, additional moving sections could be provided separate from or operatively connected to the tuft block 16 so that in addition to the vibrating section 24 there would be at least one further section with moving bristles associated with the oscillating tuft block 16.

In the illustrated embodiment tuft block 16 is a disk of circular cross-section, as is tuft block 24. Tuft block 24 could have an outwardly extending shoulder, such as shown in FIG. 3. As previously noted, the shoulder would confine tuft block 24 within head 14 to prevent the tuft block 24 from escaping from head 14 and being accidentally swallowed. The bristles 18 on tuft block 16 are shown to extend outwardly the same distance as the bristles 32 on tuft block 24 so that these moving bristles terminate in the same plane when tuft block 24 is urged to its outermost position. Fixed bristles 30 on the fixed portion 36 of head 14 are shown to terminate a shorter distance away from the outer surface 34 of the head 14. The outer surface 34 of head 14 is generally co-planar in all of its sections comprising oscillating tuft block 16, fixed section 36, as well as vibrating section 24 when vibrating section 24 is in its outermost position. The invention may be practiced where portions of the outer surface 34 extend outwardly a lesser or greater amount than other portions. Similarly, bristles 18 may extend outwardly from outer surface 34 a different length than bristles 32. Likewise, bristles 30 may extend the same distance as bristles 18 and 32 or may extend a longer distance from the outer surface 34 than other bristles. The invention may also be practiced where the bristles in each section, namely, oscillating tuft block 16, vibrating tuft block 24 and fixed section 36 have bristles of different heights and/or different inclinations to other bristles in those sections. Thus, although the drawings illustrate all of the bristles to be generally perpendicular to outer surface 34 one or more tufts of bristles may be at a non-perpendicular angle to outer surface 34 on any or all of the different sections of head 14.

In practice of the invention the fixed section 36 may have its tufts of bristles in various arrangements including completely or partially surrounding the bristles 32 of vibrating tuft block 24. If desired, fixed section 36 may have no bristles at all. The invention could also be practiced where the bristles in one section such as the fixed bristles 30 are in the form of rubber fingers for massage purposes and/or such elastomeric bristles could be provided in other sections of the head instead of or in addition to the more conventional bristle structure.

As described, tuft block 16 is driven in a back and forth oscillating rotational manner as indicated by the arrow 25 in FIG. 2. The invention may be practiced, however, where other forms of movement are utilized for tuft block 16, including a complete 360° rotational movement without any oscillation. Such practice of the invention whether tuft block 16 oscillates, rotates or moves linearly would still result in a movement in a plane generally parallel to the outer surface 34 of head 14. This parallel type movement in conjunction with the vibrating movement generally perpendicular to outer surface 34 comprises the basic practice of the invention.

Although the drawings illustrate the fixed section 36 and the vibrating section or tuft block 24 to be located between the handle neck 12 and the oscillating tuft block 16 the invention could also be practiced where the tuft block 16 is located closer to the handle neck 12 than the fixed section 36 and/or vibrating tuft block 24. Similarly, the fixed section 36 or a separate fixed section could also extend completely or partially around oscillating tuft block 16 either by reversing the location of tuft block 16 and tuft block 24 and/or extending the length of head 14.

FIG. 2 illustrates the bristles 18 in tuft block 16 to be arranged in two parallel coarcuate rows. The invention may be practiced where the tuft block is in the form of two separate tuft blocks with one row of bristles on each of the tuft blocks. Accordingly, the outer tuft block having the outer row of bristles 18 might be considered a first tuft block while the inner row of bristles might be mounted on a separate or third tuft block in addition to the second tuft block 24. The two tuft blocks having bristles 18 could be mounted for independent movement with respect to each other, to supplement the action of the tuft block 24 which has the vibrating or in and out moving bristles 32. For example, the first and third tuft blocks could oscillate in a rotational manner in directions opposite to each other by any suitable drive such as by the drive arrangement shown in U.S. Pat. No. 5,146,942 all of the details of which are incorporated herein by reference thereto.

A further variation of the invention could provide for a drive arrangement wherein the tuft block 24 oscillates or rotates in the same plane or in a parallel plane as tuft block 16, whether tuft block 16 is formed of two separate counter-oscillating tuft blocks or of a single tuft block. A rotational movement of tuft block 24 rather than the in and out movement, could be accomplished in any suitable manner such as by the provision of suitable gearing between shaft 20 and tuft block 24 so that as the shaft 20 rotates, a gear on shaft 20 would engage a gear on tuft block 24 to transmit the rotational movement of shaft 20 into a uni-directional rotational movement of tuft block 24 perpendicular to the rotational movement of shaft 20. Alternatively, tuft block 24 could be oscillated in a rotational manner similar to tuft block 16 by any suitable drive mechanism, such as by a second shaft similar to shaft 20, wherein the second shaft would drive tuft block 24 in a rotational oscillating manner while the shaft 20 also drives tuft block 16 in a rotational oscillating manner. The amplitude and/or speed of both rotational oscillating movements can differ or be the same. If desired, the sets of counter-oscillating bristles could be provided by a tuft block around tuft block 24 similar to that previously described with regard to tuft block 16 instead of, or in addition to, the counter-oscillating bristles 18 as previously described.

What is claimed is:

1. A powered toothbrush comprising a handle with a neck, a head mounted to said neck, said head having an exposed outer surface, a first tuft block mounted to a fixed section of said head, said first tuft block having bristles extending outwardly from said exposed outer surface, a first drive structure operatively connected to said first tuft block for moving said first tuft block in a plane generally parallel to said exposed outer surface, a second tuft block mounted within said fixed section of said head, at least a portion of said second tuft block being aligned with an opening in said exposed outer surface said second tuft block having bristles extending outwardly from said exposed outer surface, and said second tuft block being mounted for moving in a direction generally perpendicular to said exposed outer surface within said opening.

2. The toothbrush of claim 1 wherein said second tuft block oscillates in an in and out direction perpendicular to said outer surface to comprise a vibrating section.

3. The toothbrush of claim 2 wherein said second tuft block is free floating within said fixed section of said head.

4. The toothbrush of claim 2 including second drive structure operatively connected to said second tuft block for moving said second tuft block.

5. The toothbrush of claim 2 wherein said first tuft block is moved back and forth in an oscillating manner.

6. The toothbrush of claim 5 wherein said first tuft block is oscillated in a rotational direction.

7. The toothbrush of claim 6 wherein said head includes a fixed section having bristles.

8. The toothbrush of claim 7 wherein said fixed section completely surrounds said second tuft block.

9. The toothbrush of claim 8 wherein said bristles on said fixed section completely surround said second tuft block.

10. The toothbrush of claim 4 wherein said first drive structure and said second drive structure are part of the same drive mechanism.

11. The toothbrush of claim 10 wherein said drive mechanism includes a motor driven shaft, said shaft having a drive end which drives said first tuft block, and said shaft having a cam surface which drives said second tuft block.

12. The toothbrush of claim 7 wherein said bristles on said first tuft block extend outwardly from said outer surface the same distance as said bristles on said second tuft block when said second tuft block is in its outermost position.

13. The toothbrush of claim 12 wherein said first tuft block has a circular outer surface.

14. The toothbrush of claim 13 wherein said second tuft block is a disc with a circular outer surface and an outwardly extending shoulder.

15. The toothbrush of claim 1 wherein said head includes a fixed section having bristles.

16. The toothbrush of claim 15 wherein said fixed section completely surrounds said second tuft block, and said bristles on said fixed section completely surround said second tuft block.

17. The toothbrush of claim 15 wherein at least some of said bristles on said fixed section are fixed bristles.

18. The toothbrush of claim 15 wherein at least some of said bristles on said fixed section are embedded in an elastomeric material to have independent motion.

19. The toothbrush of claim 1 wherein said bristles on said first tuft block extend outwardly from said outer surface the same distance as said bristles on said second tuft block when said second tuft block is in its outermost position.

20. The toothbrush of claim 1 wherein at least some of said bristles are natural bristles.

21. The toothbrush of claim 1 wherein at least some of said bristles are made of elastomeric material.

22. The toothbrush of claim 20 wherein at least some of said bristles made of elastomeric material are in the form of fingers.

23. The toothbrush of claim 1 wherein a third tuft block is mounted within and separate from said first tuft block, and said third tuft block being moved in a direction generally parallel to said outer surface.

24. A powered toothbrush having a handle with a neck, a head mounted to said neck, said head having an exposed outer surface, a first tuft block mounted to a fixed section of said head, said first tuft block having bristles extending outwardly from said exposed outer surface, a first drive structure operatively connected to said first tuft block for moving said first tuft block in a plane generally parallel to said exposed outer surface, said fixed section of said head containing a plurality of fixed tufts of bristles extending from said exposed outer surface, a second tuft block mounted within and separate from said fixed section, at least a portion of said second tuft block being aligned with an opening in said exposed outer surface, said second tuft block having bristles extending outwardly from said exposed outer surface, said fixed tufts of bristles at least partially surrounding said second tuft block, and second drive structure operatively connected to said second tuft block for moving said second tuft block in a plane generally parallel to said outer surface and within said opening in said exposed outer surface.

25. The toothbrush of claim 24 including a third tuft block mounted to said head, said third tuft block having bristles extending outwardly from said exposed outer surface, and said third tuft block being movable in a direction generally parallel to said outer surface.

* * * * *